(12) United States Patent
Ellenz

(10) Patent No.: US 6,438,412 B2
(45) Date of Patent: Aug. 20, 2002

(54) MEMORY LOOP ECG RECORDER WITH CONTINUOUS RECORDING

(75) Inventor: John D. Ellenz, Olathe, KS (US)

(73) Assignee: Cardiac Evaluation Center, Inc., Milwaukee, WI (US)

( * ) Notice: Subject to any disclaimer, the term of this patent is extended or adjusted under 35 U.S.C. 154(b) by 0 days.

(21) Appl. No.: 09/681,167

(22) Filed: Feb. 7, 2001

Related U.S. Application Data (60) Provisional application No. 60/202,553, filed on May 10, 2000.

(51) Int. Cl.[7] .................................................. A61B 5/04
(52) U.S. Cl. ....................................................... 600/524
(58) Field of Search .................................. 600/523, 524

(56) References Cited

U.S. PATENT DOCUMENTS

| | | | |
|---|---|---|---|
| 4,624,263 A | * | 11/1986 | Slavin |
| 4,633,881 A | * | 1/1987 | Moore et al. |
| 5,207,219 A | | 5/1993 | Adams et al. |
| 5,282,827 A | | 2/1994 | Adams et al. |
| 5,339,824 A | | 8/1994 | Engira |
| 5,350,404 A | | 9/1994 | Adams et al. |

OTHER PUBLICATIONS

Medisana, Instructions for Cardiocheck, 7 pages.
Professor Dr. med. Bernd Kronig, Medisana, Importance of Self–Measurement, 8 pages.
Medisana Cardiocheck Self–EKG.

* cited by examiner

*Primary Examiner*—Scott M. Getzow
(74) *Attorney, Agent, or Firm*—Quarles & Brady LLP (57) ABSTRACT

An ECG recorder is provided that includes a processor configured to perform the ECG data sampling routine while performing additional routines, such as transmitting stored ECG events and setting user preferences. Accordingly, a patient's ECG signal is continuously sampled at all times during operation of the recorder.

12 Claims, 8 Drawing Sheets

MEMORY LOOP ECG RECORDER WITH CONTINUOUS RECORDING

CROSS REFERENCE TO RELATED APPLICATIONS

This application claims the benefit of the filing date of provisional patent application number 60/202,553, filed May 10, 2000, the disclosure of which is incorporated by reference as if set forth in its entirety herein.

FEDERAL RESEARCH STATEMENT

NA

BACKGROUND OF INVENTION

1. Field of the Invention

The invention relates to electrocardiographs and, more particularly, relates to a portable electrocardiograph capable of transmitting electrocardiographic signals to a remote display terminal.

2. Description of the Related Art

A cornerstone in the diagnosis of heart abnormalities is the electrocardiograph. With a typical electrocardiograph, conductive leads connect electrodes that are placed on skin of a patient to a stationary measuring machine while the patient rests on a cot or the like.

For episodic abnormalities, the electrocardiogram ("ECG") recorded by the electrocardiograph desirably covers a period of time preceding the episode ("pre-symptom data") and after the episode ("post-symptom data"). Yet immobilizing the patient during the acquisition of such pre-symptom and post-symptom data is impractical because of the general lack of predictability as to the time of occurrence of the episode. In such situations, therefore, it is known to employ a portable ECG recorder that allows the patient to be ambulatory during the measurement period. Such portable ECG equipment employs a magnetic tape to capture data during a period as long as 24 hours.

With advances in computer electronics, the so-called "memory loop recorder" has been developed. The memory loop recorder samples and digitizes the ECG signal which may then be stored as numeric values in a computer memory. Such computer memories typically have a capacity less than that obtainable by use of magnetic tape storage, however, the computer memory may be readily operated to store the ECG signal in a loop fashion over an indefinite period of time. For example, at any given time the memory loop recorder might store the last twenty minutes of ECG data. Newly arriving data continues to replace the oldest data in the memory.

The patient is provided with a control that is to be activated when an episodic abnormality is detected. At this time the recording continues for a predetermined time and then stops so that the memory holds both pre- and post-symptom data.

As any episodic cardiac abnormality may prove to be life-threatening, it is desirable to have the recorded ECG data reviewed by an electrocardiographer as soon as possible. In this regard, it is known to employ telephone line for the transmission of recorded ECG data to a remote display device where it can be reviewed and analyzed. In such systems, the stored ECG data is played back over the telephone line from beginning to end so that the electrocardiographer can view the progression of the abnormal episode.

At certain times, such as when conventional ECG recorders are performing tasks associated with standard operation, real-time recording of ECG data will not be possible. For instance, real-time ECG data is not sampled during a series of self tests, which typically occur once the patient decides to erase previously stored data after transmission to clear up the memory. Additionally, ECG data is not sampled while the user is programming various preferences into the recorder. Furthermore, conventional recorders are incapable of sampling real-time ECG data either during or immediately after stored ECG events are transmitted to the electrocardiographer. It is easily appreciated that any ECG episodes experienced by the patient during these times will not be recorded and, consequently, will not be examined.

What is therefore needed is an ECG recorder that is capable of performing the necessary tasks associated with operation while sampling real-time ECG data without interruption.

SUMMARY OF INVENTION

The present invention allows sampling of electrocardiographic data while performing other tasks associated with operation in a functionally concurrent manner.

An apparatus for recording electrocardiographic data from a patient includes an acquisition circuit operable to receive at least one electrocardiographic signal having a time-varying amplitude from the patient at a plurality of instants in time to produce samples and further digitizing the samples of the electrocardiographic signal to indicate the amplitude of the electrocardiographic signal at the plurality of instants to produce digitized samples, at least one memory operable to receive and store the digitized samples according to their associated sampling instants in time, and a processor communicating with the acquisition circuit and the memory to transfer the digitized samples from the acquisition circuit to the memory as a first task while executing a second task on a functionally concurrent basis, wherein the second task is selected from the group consisting of transmitting electrocardiographic data and setting user preferences.

These as well as other features and characteristics of the present invention will be apparent from the description which follows. In the Detailed Description below, preferred embodiments of the invention will be described with reference to the accompanying drawings. These embodiments do not represent the full scope of the invention. Rather the invention may be employed in other embodiments, and reference should therefore be made to the claims herein for interpreting the breadth of the invention.

BRIEF DESCRIPTION OF DRAWINGS

Reference is hereby made to the following figures in which like reference numerals correspond to like elements throughout, and in which.

DETAILED DESCRIPTION

Figure 1:
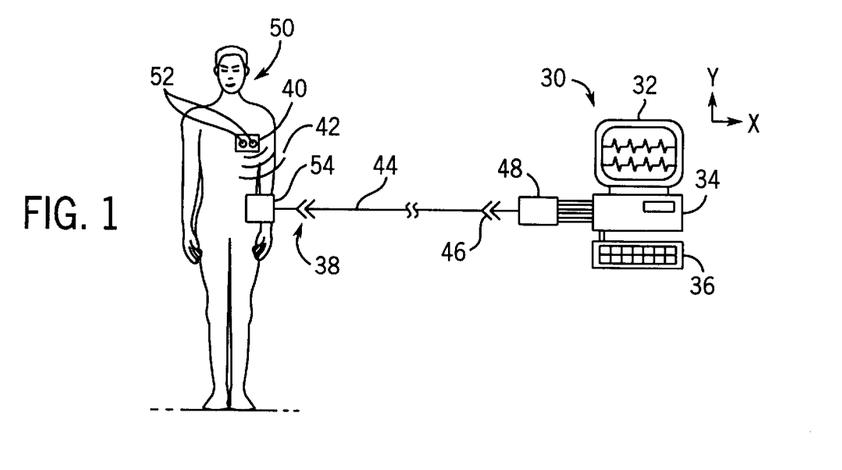
FIG. 1 is an illustration of the principal components of the preferred embodiment including the electrodes, the recording unit, and the remote display terminal.

Referring initially to FIG. 1, an electrode assembly 40, attached to a patient 50, includes multiple electrodes 52 positioned to receive to two channels of electrocardiographic data as is generally understood in the art. A lightweight recording unit 54 is carried by the patient 50 via a pocket, pouch, lanyard, harness, or the like (not shown) and positioned in proximity with the electrode assembly 40 to receive the electrocardiographic data from the electrodes 52.

In the preferred embodiment, the electrode assembly may be connected to the recording unit 54 with conventional flexible wire leads. In accordance with an alternate embodiment, the electrode assembly 40 may communicate the electrocardiographic data to the recording unit 54 by low powered radio waves. Wireless transmission of ECG data is well known in the art and wireless electrode assemblies 40 suitable for use with the present invention are commercially available from Transkinetics located in Canton, Mass. A wireless electrode assembly 40 provides the patient 50 with improved mobility.

The recording unit 54 may be connected to voice grade telephone line 44 by jack 38 for transmitting or receiving data. Principally, the telephone line 44 carries electrocardiographic data from the recording unit 54 to a remote display terminal 30 where it is received by interface unit 48 connected to the telephone line 44 by jack 46. The remote display terminal 30 includes a display 32, a computer 34 and a keyboard 36, and may be a personal computer such as is well known in the art and commercially available through a variety of vendors.

The interface unit 48 also transmits data from the remote display terminal 30 and communicates that data via telephone line 44 to the recording unit 54. Such data is used to configure the recording unit 54 as will be described below and provides for control of data transfer from the recording unit 54 by an operator at the remote display terminal 30. One such embodiment of the electrodes 52, the recording unit 54, and the remote display terminal 30 is described in U.S. Pat. No. 5,339,824, the disclosure of which is hereby incorporated by reference.

Figure 2:
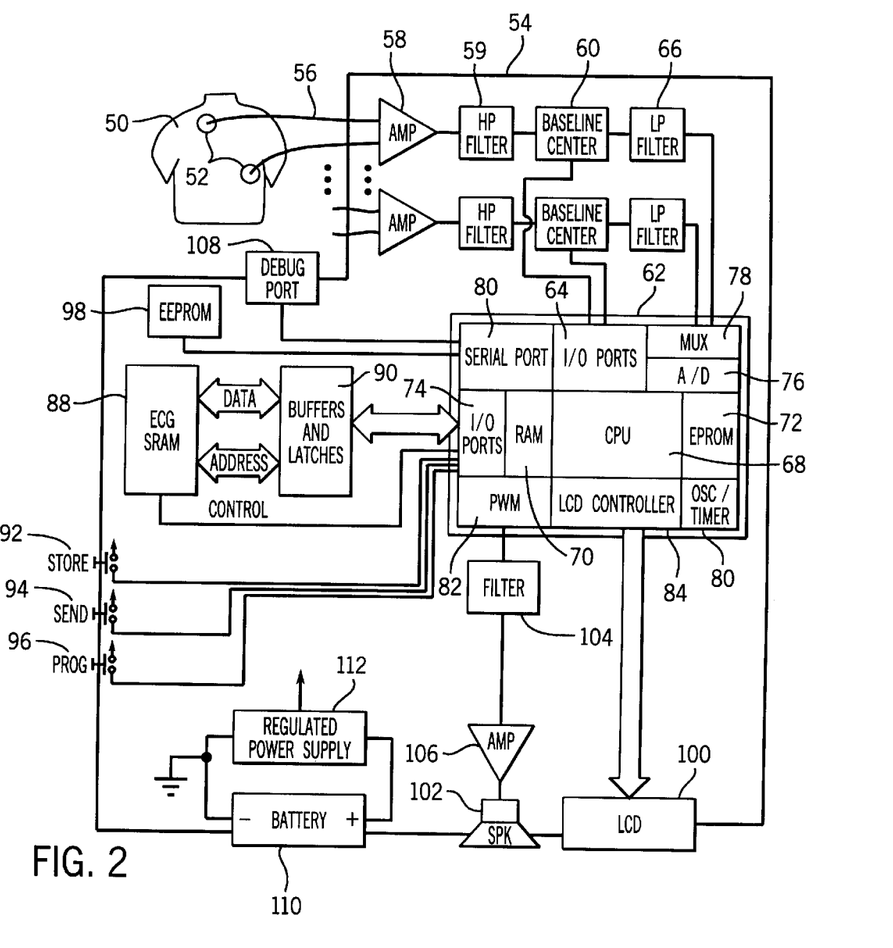
FIG. 2 is a block diagram of the recording unit and electrodes of FIG. 1.

Referring now to FIG. 2, in one embodiment, the recording unit 54 is connected to the electrodes 52 via a cable assembly 56, and is carried in close proximity to the patient 50. The cable assembly 56 is connected to one or more differential amplifiers 58, which remove common mode noise from the signal collected from the electrode 19 and additionally provide gain to the ECG signals. Each channel of ECG data is then passed from the amplifier 58 to a base line centering circuit 60 which includes both a high pass filter 59 for removing the DC components of the signals, as well as a digitally controlled switch which raises the cutoff frequency of the filter. The switch is activated by a one chip microprocessor 62 via I/O ports 64 during periods of amplifier saturation to allow fast recovery of the amplifiers 58. The signal is then sent from the base line centering circuit 60 into a low pass filter 66 that removes unwanted high frequency noise, thereby allowing for digitization of the signal without aliasing.

The recording unit 54 includes the microprocessor 62 having a CPU 68 connected by an internal bus to an internal random access memory 70 ("RAM"), an erasable programmable read-only memory 72 ("EPROM"), and I/O ports 64 and 74. The internal bus also connects the CPU 68 to an acquisition circuit, including an A to D converter 76 which receives inputs from an analog multiplexer 78. It should be appreciated that the acquisition circuit could further include a memory for the temporary storage of ECG data, as would be appreciated by those having ordinary skill in the art. The internal bus further connects the CPU 68 to a serial port 80, PWM 82, LCD controller 84, and oscillator/timer combination 86 which controls the sampling rate of ECG data by providing a periodic interrupt input to the CPU 68 which allows the CPU 68 to respond to the ECG input on a real-time basis, as will be described in more detail below. Such microprocessors are well known in the art and may be obtained commercially from Microchip Technologies of Chandler, Ariz.

The channels of filtered ECG data sent from the filters 66 are received by the inputs of the multiplexer 78 which, under the control of the CPU 68, samples the channels of ECG data alternately in rapid succession, which are subsequently digitized by the A to D converter 76. The rate of digitization of the ECG data is 480 samples per second per channel in accordance with the preferred embodiment.

Once digitized, the ECG data is further filtered by a digital filter implemented within the software of the microprocessor 62 so as to remove in-band Gaussian noise by, for example, an infinite impulse response filter or finite impulse response filter as is understood to those of ordinary skill in the art. Alternatively, the filter may be a median-type filter for the removal of noise. The added filtering in the software of the microprocessor 62 results in a further reduction of signal bandwidth which allows the ECG data to be accurately represented by a low sampling rate, which is 120 samples per seconds in accordance with the preferred embodiment.

In accordance with an alternate embodiment, the A to D converter 76 may be a low power version of the sigma delta type, which may be obtained commercially from Analog Devices of Norwood, Mass. This type of converter, as is understood to those of ordinary skill in the art, provides high resolution sampling of small signals over a large dynamic range, thereby allowing the converter 76 and subsequent digital processing by the microprocessor 62 to replace much of the gain, filtering, and centering functions found in the amplifier 58, centering circuit 60, and filter 66.

The filtered ECG data is then transmitted over the I/O port 74 and are stored in an ECG static random access memory ("SRAM") 88. The SRAM in accordance with the preferred embodiment contains 131,072 8-bits storage locations, and is the type commercially from Toshiba America located in Irvine, Calif. Buffers and latches 90 are disposed between the SRAM 88 and I/O port 74 to demultiplex the address and data information from the I/O port 74 that is to be stored in the SRAM 88. The buffers and latches 90 operate under the control of CPU 68, as is understood by those of ordinary skill in the art.

Operation of the recording unit 54 is controlled by three user-activated buttons: the store button 92 which signals the recording unit 54 to store the current ECG episode, the send button 94 which signals the recording unit to begin transmitting previously stored ECG episodes to a remote terminal; and the program button 96 which signals the recorder to enter a program mode to allow a user to set user preferences such as episode duration and number. Furthermore, the patient 50 may specify the order in which the stored ECG data blocks are to be transmitted (e.g. first-in, last-out; or last-in, first-out). The user preferences are stored in an electrically erasable programmable read-only memory ("EEPROM") 98, which is nonvolatile to retain the user preferences until such time as the user sees fit to change them. The store, send, and program features will be described in more detail below.

The user interface required on the recording unit 54 in accordance with the preferred embodiment has been minimized to include the store, send, and program buttons 92, 94, and 96, respectively, and an LCD 100 that operates under instructions provided by LCD controller 84 for user feedback purposes. The recording unit 54 further includes a piezoelectric speaker 102 that transmits stored ECG data sent from the PWM 82 via a low-pass filter 104 and power amplifier 106. In addition, the speaker 102 may provide the patient 50 with a status update, for example if the patient attempts to erase data before transmitting, or if the SRAM 88 is full. As will be described in more detail below, the storage of ECG data and the other functions of the recording unit 54 are controlled by the CPU 68 under the control of firmware.

The recording unit 54 continuously samples and temporarily stores real-time episodic data acquired from electrodes 54, such that the oldest data is replaced with the most recent data. The patient 50 activates the store button 92 in response to, for example, an abnormal episode such as an arrhythmia to store the corresponding ECG data. Alternatively, the recording unit 54 may be configured to automatically detect an abnormal episode and store the corresponding electrocardiographic data in the SRAM 88. This will signal the recording unit 54 to permanently store the current real-time data so as to permit the patient 50 to transmit that data to a remote terminal at a later time. It should be appreciated that the recording unit 54 will store both pre-symptomatic data as well post-symptomatic data to ensure that the entire abnormal episode is recorded for future transmission. As will be described in more detail below, the real-time ECG data is continuously recorded even as other processes are being executed, thereby assuring that all abnormal events are recorded for future transmission.

Activation of the store button 92 signals the microprocessor 62 to save the current ECG loop. The software in EPROM 72 then initiates and controls the storage by marking the pre-symptomatic data for the episode already contained in the current ECG loop in SRAM 88 and by continuing to save post-symptomatic ECG data to the SRAM 88. When a suitable amount of post-symptomatic data has been collected, the entire episode in the current ECG loop will be marked as a stored event in the SRAM 88 and subsequent collection will store data in an unused region of the SRAM. The store operation could also be initiated by an ECG analysis function of the software that automatically detected an arrhythmia as is known in the art. For example, such algorithms are incorporated into recorders of this type and are commercially available from Alaris Medical Systems, San Diego, Calif.

In response to the activation of send button 94, the microprocessor 62 begins transmitting the stored ECG data to the remote display terminal 30. The mode of transmission in accordance with the preferred embodiment is frequency modulation ("FM") about a carrier frequency of nominally 1900 hertz with a deviation of 100 hertz per one milivolt of ECG amplitude, and is performed by the digitally controlled oscillator 88. Oscillator 88 calculates amplitude points on a modulated sign wave representing the modulated ECG signal, having points that are converted into analog voltages with the PWM 82 at a rate of 14,400 hertz. The signal is then passed through the low pass filter 104 and then to the power amp 106 which drives the piezoelectric speaker 102. The patient 50 may then hold the speaker next to the mouthpiece of a telephone when transmitting data to the remote display terminal.

Alternatively, the FM modulation may occur external to the microprocessor 62 using either an analog modulator or a second microprocessor performing the DCO function. Additionally, the ECG data may alternatively be stored in EEPROM 98, FLASH or any other suitable nonvolatile storage to protect that data against power failure. Such devices are currently available having interface requirements compatible with SRAM 88 from Advanced Micro devices located in Sunnyvale, Calif.

Figure 3:
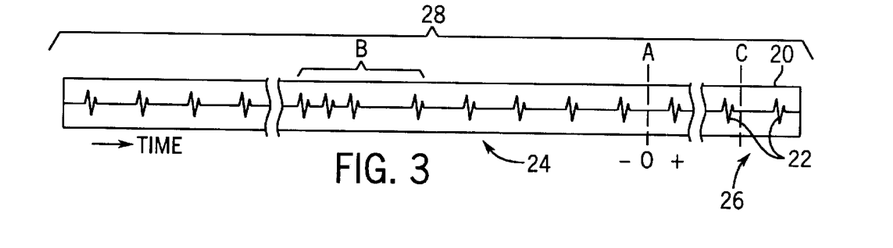
FIG. 3 is a schematic representation of an ECG signal as stored in accordance with the preferred embodiment identifying an arrhythmic episode.

Referring now to FIG. 3, ECG data 20 as might be recorded by recording unit 54 includes a plurality of QRS complexes 22 indicating the contraction of a human heart. Typically such QRS complexes 22 are regularly spaced but under certain circumstances they may exhibit arrhythmic behavior indicated generally by area B.

Such arrhythmias B may be recognized by the patient 50 at instant A at which time store button 92 (shown in FIG. 2) is pressed by the patient 50. ECG data 20 occurring prior to instant A is termed pre-symptom 24 and data occurring after instant A is termed post-symptom data 26.

As discussed above, the recording unit 54 may be programmed to store a predetermined amount of pre-symptom and post-symptom data 24 and 26 which together determine a loop length 28.

Figure 4:
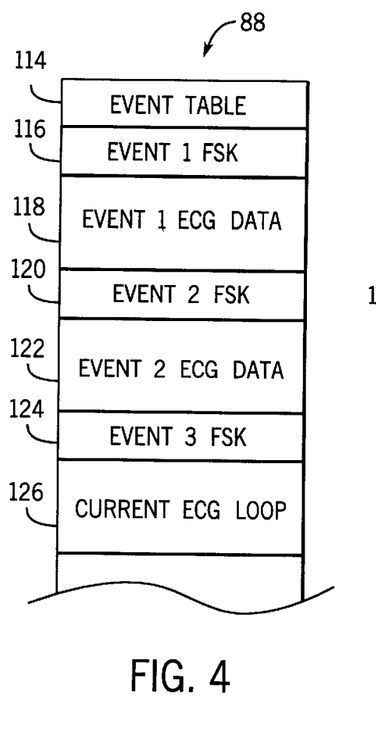
FIG. 4 is a schematic illustration of the event table of the static random access memory illustrated in FIG. 2.

Referring now to FIG. 4, the SRAM 88 is partitioned into an event table 114 having a plurality of address pointers and channel information for all stored events as well as a current ECG loop 126 for storing real-time ECG data. A plurality of event blocks 118 and 120 are included in the event table and store saved episodes for future transmission. While only two such event blocks are illustrated, it should be appreciated that the SRAM 88 includes as many blocks as possible up to capacity. A reserve portion of event blocks (not shown) are also included for storing events after the patient has been alerted of a memory low condition. Each ECG data block 118, 122 and 126, has a corresponding frequency shift keying (FSK) block 116, 120, and 124, respectively, containing time offsets and other data that are used when transmitting ECG data.

Figure 5:
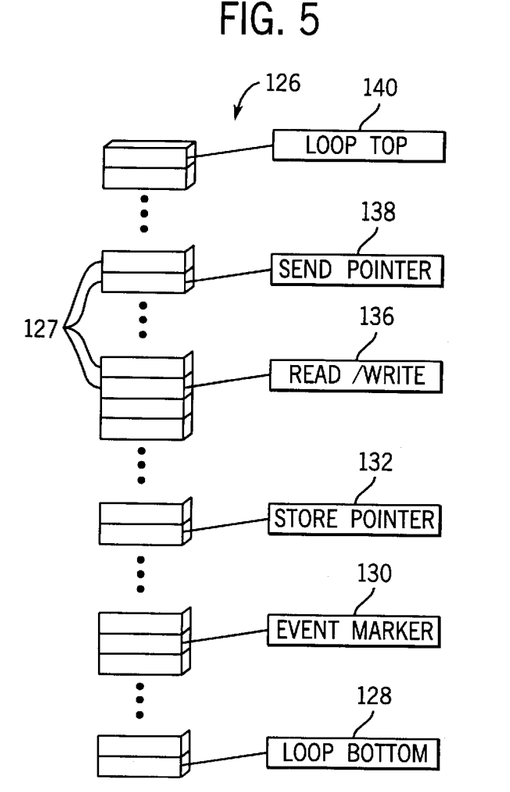
FIG. 5 is a schematic illustration of the event loop of the event blocks illustrated in FIG. 4.

Referring now to FIG. 5, the real-time ECG loop data block 126 includes a plurality of pointers that allows the user to update real-time data and store an episode in one of the event data blocks for future transmission. In particular, the ECG loop block 126 includes a loop bottom address 128 and a loop top address 140, which define the position of the ECG loop block within the SRAM 88, and which are separated by a value equal to twice the loop length in seconds times the sampling rate.

Once the recording unit 54 is programmed, it begins accepting ECG data from the electrode assembly 40. At each of the addresses 127 of SRAM 88 between the loop top address 140 and the loop bottom address 128 an ECG signal sample is stored starting at the loop bottom and progressing in sequence to the loop top. A read/write pointer 136 is incremented twice after the storage of each ECG sample (for each of the two channels of ECG data) to track the address at which the next sample should be stored. When the read/write pointer 136 equals the loop top address 140, the pointer 136 is set equal to the loop bottom address 128 and new ECG signals are stored over the old ECG samples. This process repeats indefinitely to provide a constant window of stored ECG data equal to the loop length. A symbolic marker (not shown) is also saved in memory locations in close proximity to the time the event was detected to provide a visual reference for the electrocardiographer.

When the patient 50 experiences an abnormal episode, B, (shown in FIG. 3), or if the episode is automatically detected, an event marker 130 will indicate the address of the ECG sample received at the instant B. A store pointer 132 in SRAM 88 will indicate the address of the ECG sample received at the instant A and will sequentially store subsequent ECG samples in an open event block until all post-symptomatic data C has been stored.

Figure 6:
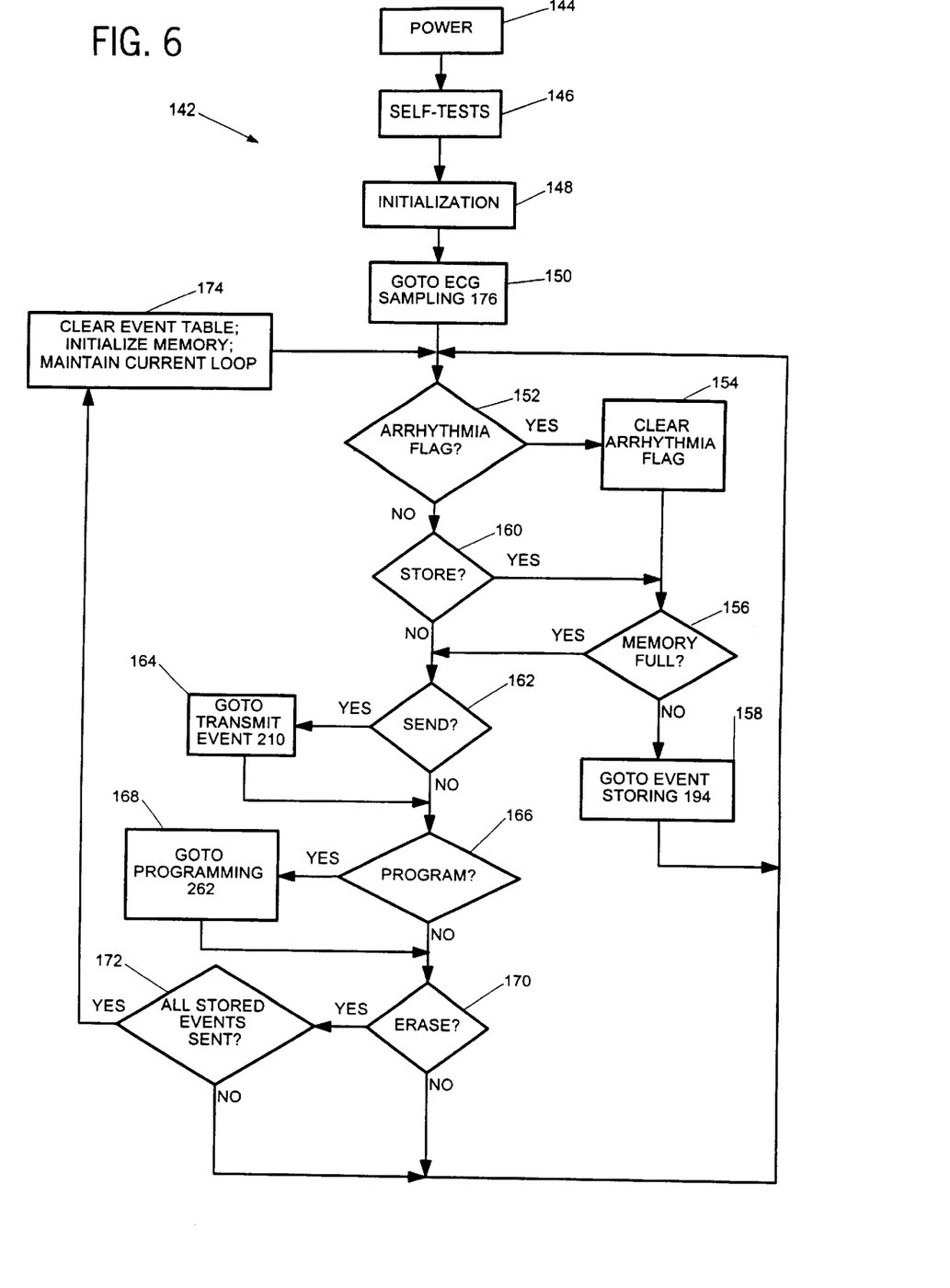
FIG. 6 is a flowchart of the routine executed by the recording unit illustrated in FIG. 2.

Referring now to FIG. 6, the various functions of the recording unit 54 are performed by the CPU 68 under the control of FIRMWARE to execute an operating routine 142. The routine 142 begins at step 144, where the patient 50 or other user activates a power mechanism (not shown) to power-up the recording unit 54. Next, at step 146, when the recorder 54 begins operation in normal operating mode, a series of self-tests is performed to confirm the integrity of the system components, such as SRAM 88, the bus interfaces, timers, and ECG amplifiers. Next, at step 148, the peripherals and memory are initialized, and the user parameters are read from EEPROM 98 which will determine the partitioning of SRAM 88.

Figure 7:
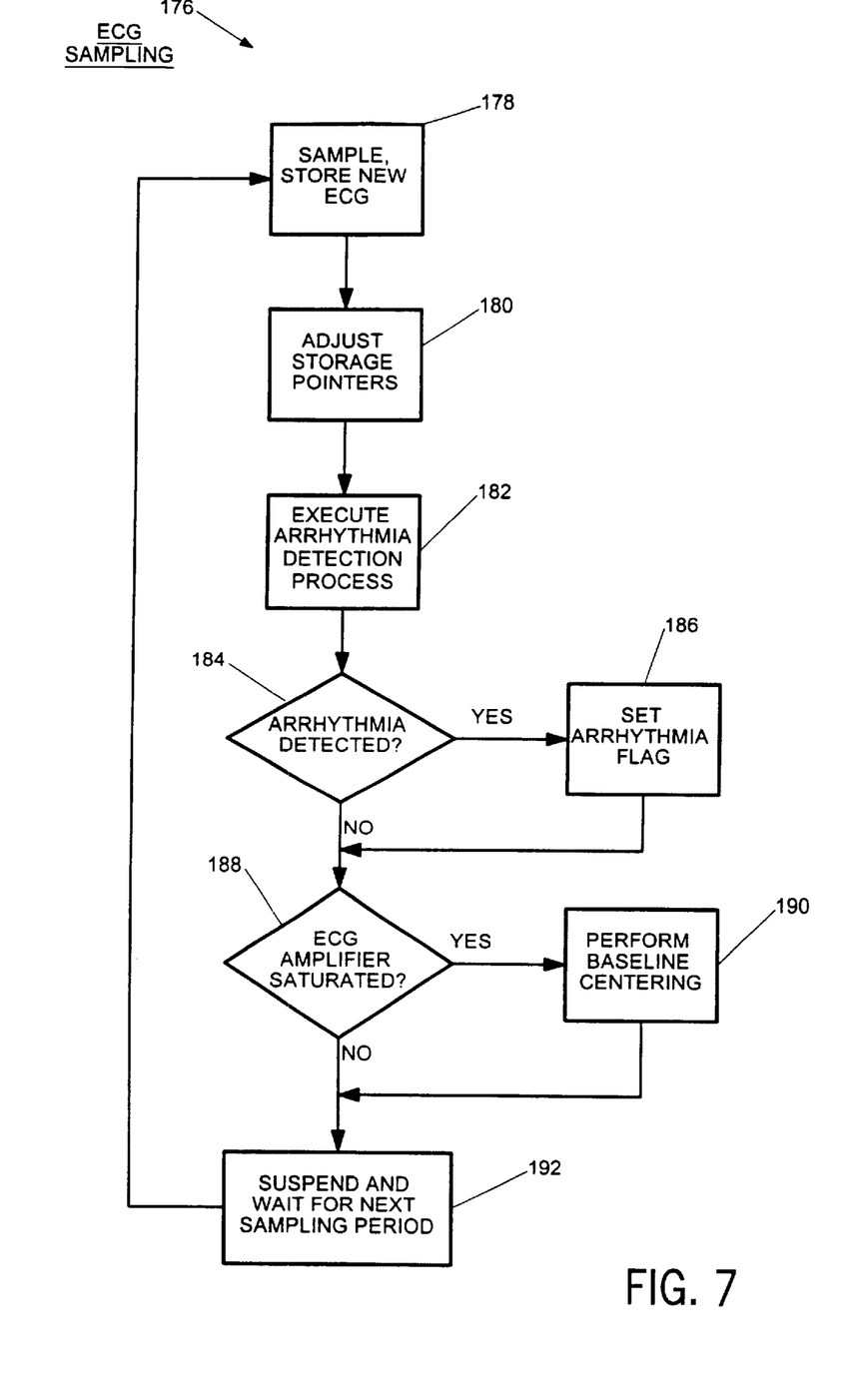
FIG. 7 is a flowchart of an ECG sampling sequence executed during the routine illustrated in FIG. 6.

Referring now to FIG. 7, at any point during routine 142, processor 68 may receive an interrupt to perform an ECG sampling routine 176, as will be described in more detail below. The interrupt occurs at a frequency sufficient to ensure that all real-time ECG data is sampled.

The routine 176 begins at step 178, where the ECG data from patient 50 is digitized and stored in an appropriate ECG data block 118 designated for the current loop as described above with reference to FIGS. 4 and 5. An automatic arrhythmia detection process 182 is performed in accordance with the preferred embodiment at step 182, as is known to those having ordinary skill in the art. If it is determined at decision block 184 that an arrhythmia was detected, the routine 176 proceeds to step 186 whereby an arrhythmia flag is set for use by the routine 142, as will be described in more detail below. Once the flag is set at step 186, or if no arrhythmia is detected at decision block 184, the routine 176 proceeds to decision block 188, where it is determined whether the ECG amplifier is saturated. If saturation is not detected at decision block 188, the routine 176 continues to step 192 where the CPU 68 awaits the next sampling. Otherwise, if the ECG amplifier is determined to be saturated at decision block 188, a baseline centering operation 190 is performed prior to the next sampling period to correct for the saturation. The routine 176 then returns from the interrupt to routine 142 at step 192.

Routine 142 may execute the sampling routine 176 at predefined intervals using, for example, a periodic hardware interrupt, or isosynchronous programming whereby the code for routine 176 is explicitly called for, as is well known to those having ordinary skill in the art. In accordance with the preferred embodiment, an interrupt timer (not shown) operates at 480 Hz, while ECG input is sampled at 120 Hz and ECG output is sampled at 14,400 Hz. The sampling routine 176 therefore continues to iterate during all modes of recording unit operation, and because routine 176 is performed at a rate sufficiently greater than the rate at which ECG data is sampled, continuous recording of a patient's ECG data is provided. Accordingly, ECG data is continuously sampled during and after the transmission of stored events as well as during the programming of user preferences, as will be described in more detail below.

The CPU 68 is thus configured to multiplex between various modes of operation. While no two sequences are performed simultaneously in accordance with the preferred embodiment, it should be appreciated that the frequency at which data is sampled is such that the sampling routine 176 is performed functionally concurrently with other tasks, such as a transmit sequence 210 during which ECG data is transmitted to a remote location, such as an electorcardiographer, and programming sequence 262 during which user preferences are set, as will be described in more detail below. Additionally, ECG data is sampled immediately after the transmit sequence 210 is executed, contrary to conventional recorders, thereby maintaining the integrity of the sampled ECG data. Accordingly, because all ECG data is being sampled at predetermined intervals such that no data is lost even during the execution of other routines, the sampling is said to be carried out functionally concurrently with those routines. It should further be appreciated that, while a single processor is used to multiplex during these various modes of operation in accordance with the preferred embodiment, functional concurrence could alternatively be achieved using a second processor that performs the sampling routine 176 at predetermined intervals. Referring again to FIG. 6, after completion of the ECG sampling routine 176, it is determined at decision block 152 whether the arrhythmia flag has been set. If so, the flag is first cleared at step 154. Next, if it is determined at decision block 156 that the SRAM 88, including the event blocks and reserve memory, is not full, then the routine 142 proceeds to an event storing sequence 194 at step 158. Alternatively, if it is determined at decision block 152 that the arrhythmia flag is not set, the routine 142 determines at decision block 160 if the store button 92 has been manually activated. If so, the memory is checked at decision block 156 before proceeding to the event storing sequence 194.

Figure 8:
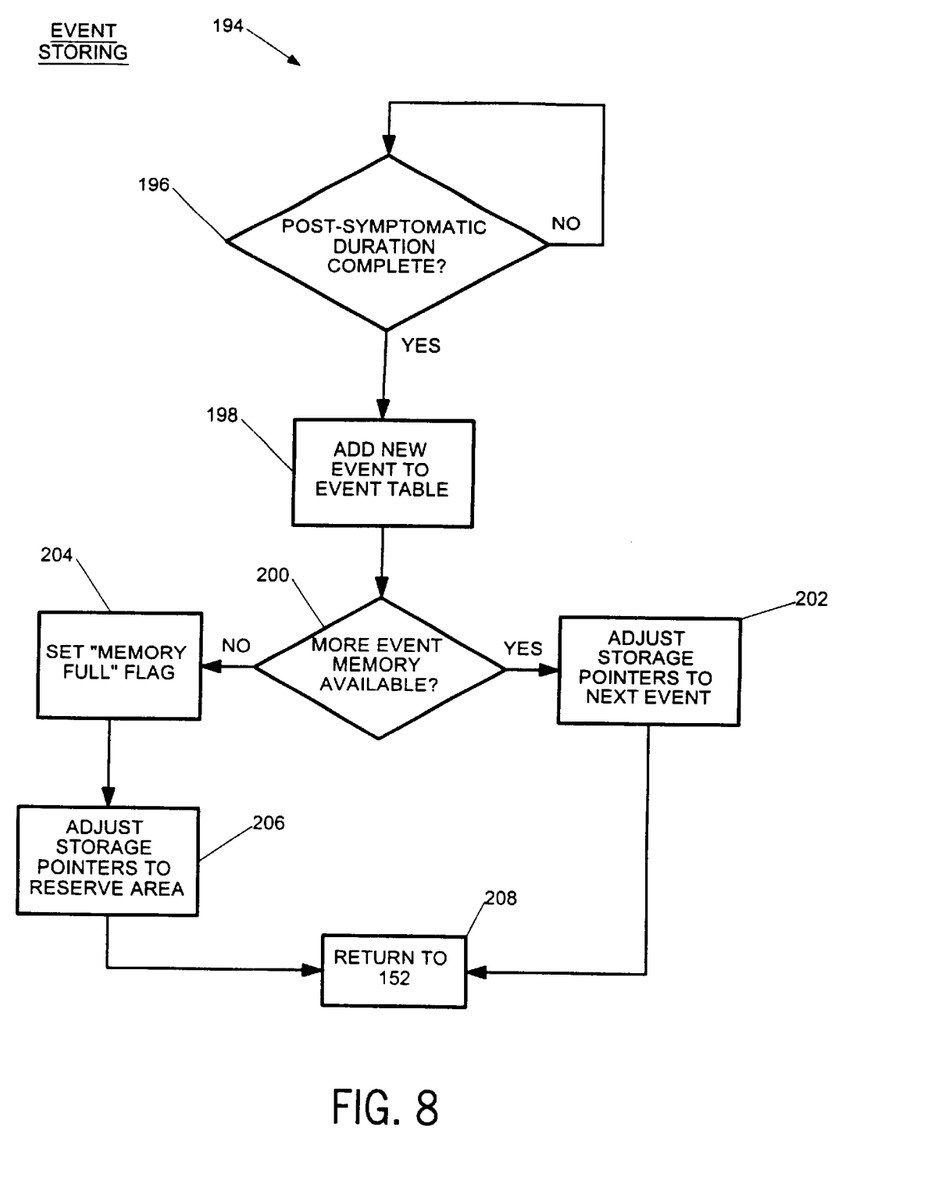
FIG. 8 is a flowchart of an event storing sequence executed during the routine illustrated in FIG. 6.

Referring now to FIG. 8, sequence 194 begins at decision block 196, where it is determined whether a predetermined amount of post-symptomatic ECG data has been received. If not, sequence 194 waits until that data has been collected before proceeding to step 198, where the abnormal event is added to the event table 114. Accordingly, decision block 196 allows the store pointer 132 to advance only a predetermined number of additional addresses for the acquisition of new ECG data as determined by the post symptom time stored in EEPROM 98 and programmed by the patient 50. When the store pointer has advanced by the proper number of addresses, the event is marked as saved by storing its addresses in the event table at step 198. The store pointer 132 is adjusted to identify the next empty event block in SRAM 88. With the event stored in the SRAM 88, new real-time data may be stored in the event loop 126 while the ECG data corresponding to the arrhythmia is saved for future transmission.

Next, at decision block 200, it is determined whether additional event blocks are available in SRAM 88 for the storing of a subsequent event. If so, the store pointer 132 is adjusted to identify the next empty event block in SRAM 88. Sequence 194 then proceeds to step 208, where the arrhythmia flag and, alternatively, the store button 92 are once again examined at steps 152 and 160, as it is appreciated that the ECG sampling routine 176 continues to execute at predetermined interrupts even during the execution of the event storing sequence 194.

If, alternatively, it is determined at decision block 200 that no event blocks are available in SRAM 88, a memory full flag is set at step 204 which will alert the patient 50 that the stored ECG data should be transmitted and erased to free-up memory space for the storing of subsequent events. Such an alert could be broadcast, for example, via speaker 102 or a visible indicator. As described above, the SRAM 88 includes a reserve area that is configured to store a finite number of events after it is determined that the main memory is full at decision block 200. Accordingly, the patient 50 will have adequate time to transmit the stored ECG data without losing the opportunity to store a number of subsequent events. Once the memory full flag is set, the event storing sequence 194 proceeds to step 206, where the storage pointer 132 is set to identify an open portion of the reserve area. The sequence 194 then proceeds to step 208, which returns the process to step 152 in FIG. 6.

If an event is not detected, or if it is determined that the SRAM 88 is full at decision block 156, routine 142 proceeds to decision block 162, where it is determined whether the user has activated the send button 94. If so, routine 142 proceeds to a transmit event sequence 210 at step 164. To initiate ECG data transfer from the recording unit 54, the patient 50 contacts an operator at a remote display terminal using a telephone handset or other equivalent mode of communication, such as the internet or e-mail. The patient 50 is then instructed to activate the send button 94, which is detected at decision block 162. At step 164, routine 142 executes a transmit event sequence 210.

Figure 9A:
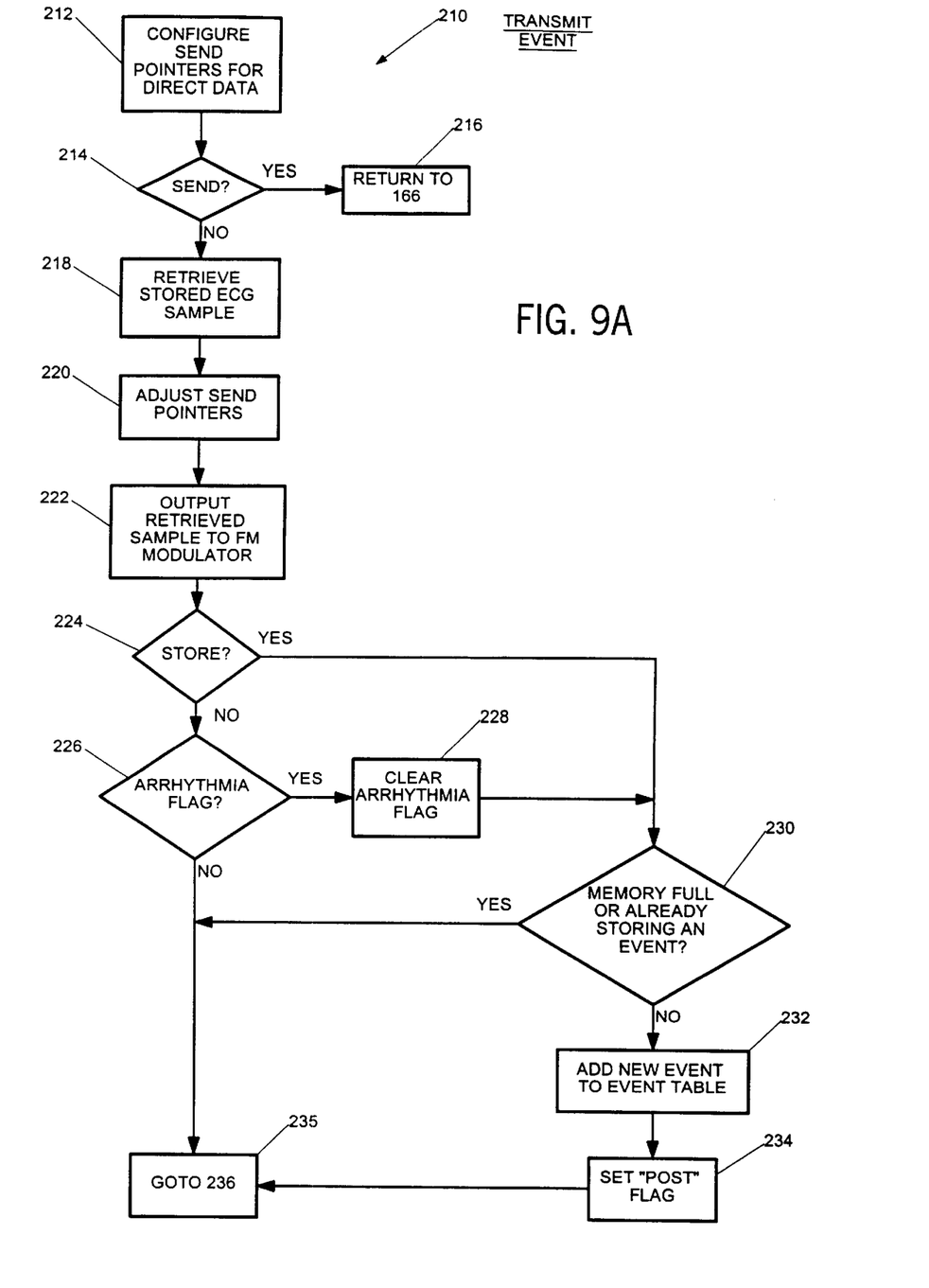
FIG. 9A is a flowchart of the first portion of a transmit event sequence executed during the routine illustrated in FIG. 6.

Referring now to FIG. 9A, the transmit event sequence 210 begins at step 212 where the send pointer 138 is set to the start of the most recently collected data. As will be described in more detail below, the patient 50 is able to program the recording unit 54 to transmit the most recent real-time data along with any stored events. If the patient 50 chooses this option, the most recent 30 seconds of ECG data, for example, is identified by the send pointer 138 in accordance with the preferred embodiment. Next, at decision block 214, if the send button 94 has been pressed again, the sequence 210 will abort at step 216, and return to step 166 of FIG. 6 as if the send button had never been pressed. Thus, the patient 50 is able to abort the transmission after the send button 94 has already been depressed.

If, however, the send button is not depressed at decision block 214, the sequence 210 proceeds to step 218, whereby the ECG data identified by the send pointer 138 is retrieved. The send pointer 138 is then adjusted to identify the subsequent ECG sample at step 220, and the ECG sample that was retrieved at step 218 is then FM modulated for transmission at step 222. The CPU 68 performs the modulation by implementing a digitally controlled oscillator (DCO), which operates by maintaining a phase accumulator whose rate of phase change is controlled by the desired FM frequency as is understood by those having ordinary skill in the art. ECG samples representing the amplitude of the FM modulated signal are sent to the PWM 82, which converts the signal from digital to analog.

The sequence 210 then determines at decision block 224 whether the patient 50 has activated the store button 92, thereby indicating an abnormal event. If the store button 92 has not been pressed, it is determined at decision block 226 whether the arrhythmia flag has been set, as it is appreciated that the ECG sampling routine 176 is being constantly executed at predetermined intervals, as described above. If it is determined that the arrhythmia flag is set, the flag is cleared at step 228 before proceeding to decision block 230. Additionally, if it is determined at decision block 224 that the store button has been pressed, the sequence 210 will proceed to decision block 230, where it is determined whether the SRAM 88 is full or already storing an event. If the store button is not pressed at decision block 224, and if the arrhythmia flag is not detected at decision block 226, the sequence 210 will proceed to decision block 236, as will be described in more detail below.

Figure 9B:
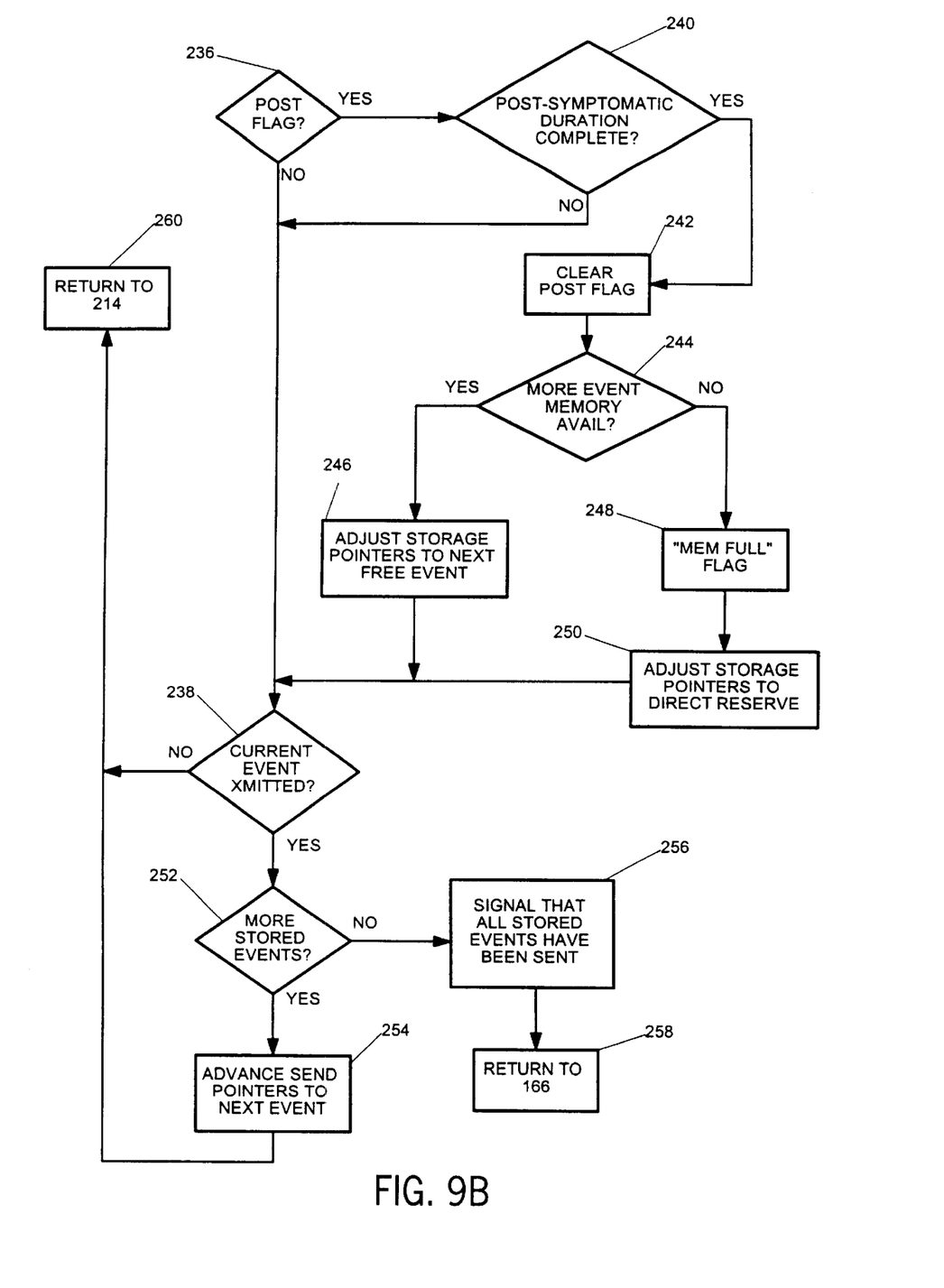
FIG. 9B is a flowchart of the second portion of the transmit even sequence illustrated in FIG. 9A.

If the SRAM 88 has memory available, the new event will be added to the event table 114 at a location in the SRAM that is defined by the store pointer 132 at step 232. A post flag is then set at step 234, indicating that post-symptomatic data of the event is being stored in the SRAM, before proceeding to decision block 236, as shown in FIG. 9B. Alternatively, if it is determined at decision block 230 that the SRAM 88, including the reserve memory, is full or already storing an event, the sequence 210 will proceed to decision block 236.

If the post flag is set at decision block 236, sequence 210 proceeds to decision block 240, where it is determined whether the post symptomatic duration has been completed as defined in the user preferences. If the post-symptomatic duration is completed, the post flag is cleared at step 242, and sequence 210 proceeds to decision block 244 where it is determined whether additional blocks are available in SRAM 88. If so, the storage pointer 132 is adjusted to identify the next free event in the SRAM 88. Otherwise, the memory full flag is set at step 248 to alert the patient 50.

Next, at 250, the storage pointer 132 will be adjusted to identify a storage location in the reserve portion of SRAM 88. Once the storage pointer has been adjusted at either step 246 or 250, sequence 210 will proceed to decision block 238, where it is determined whether the current event has been transmitted. Alternatively, if the post flag has not been set at decision block 236, the sequence 210 will proceed directly to decision block 238.

If the current event has not been transmitted, sequence 210 returns to decision block 214 to once again retrieve and output the stored ECG sample to the FM modulator, assuming that the patient 50 has not aborted the sequence 210 by once again depressing the send button 94. If, on the other hand, it is determined that the current event has been transmitted at decision block 238, it is then determined at decision block 252 whether there are more stored event to be transmitted. If so, the send pointer 138 will be advanced to the next event in the SRAM 88 that is to be transmitted. The sequence 210 will then return to decision block 214 as described above. Once it is determined at decision block 252 that all stored events have been transmitted, the patient 50 or, alternatively, the remote terminal will be alerted that all stored event have been transmitted at step 256. At step 258, the transmit event sequence 210 returns to decision block 166, as illustrated in FIG. 6. It should be appreciated that routine 142 is configured to receive the event storing interrupt throughout and after sequence 210. Accordingly, the patient's real-time ECG data will not be lost due to updating procedures that occur after transmitting as in conventional ECG recorders.

Referring again to FIG. 6, if it is determined at decision block 162 that the patient 50 has not activated the send button 94, routine 142 will proceed to decision block 166, where it is determined whether the program button 96 has been activated. If so, at step 168, routine 142 proceeds to programming sequence 262, as will now be described with reference to FIG. 10.

Figure 10:
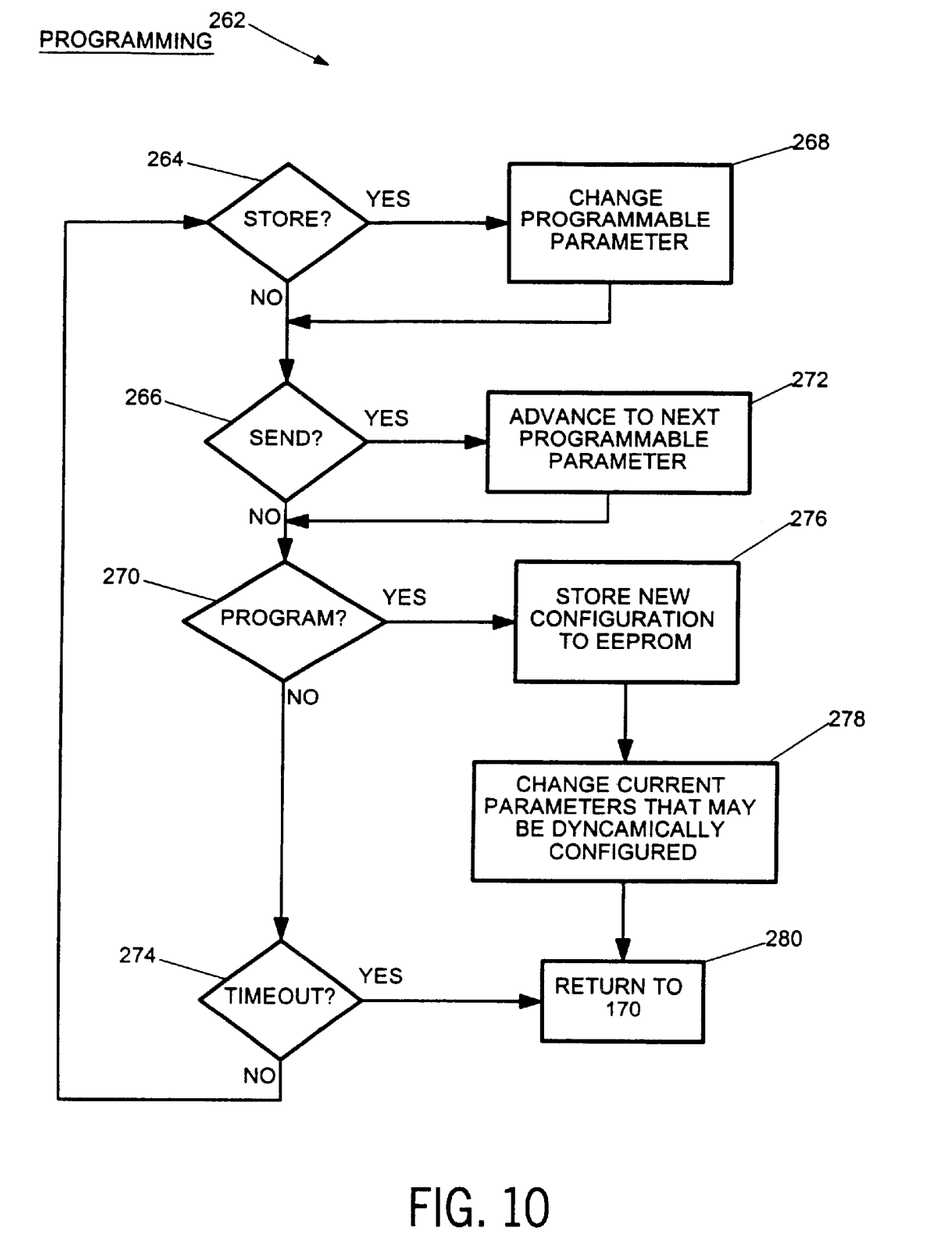
FIG. 10 is a flowchart of a programming sequence executed during the routine illustrated in FIG. 6.

In particular, a number of user preferences are identified as parameters that may be configured by the user. During programming mode, the store, send, and program buttons 92, 94 and 96, respectively, assume specialized functions as will now be described.

To begin, at decision block 264, it is determined whether the store button 92 has been activated by the patient 50. If so, sequence 262 will allow the patient to change the settings of the user preference currently displayed at step 268. After step 268, or if it is determined that the store button 92 has not been activated, sequence 262 advances to decision block 266.

If, at decision block 266, it is determined that the patient 50 has activated the send button 94, the sequence will advance to the next user preference at step 272 so that the patient can view and change that setting if so desired. Examples of user preferences implemented in accordance with the preferred embodiment include the length of each stored event (including pre-symptomatic and post-symptomatic data), activation of various warning tones (such as a low battery indicator), and ability to sample either one or two channels of ECG data.

After step 272, or if it is determined at decision block 266 that the send button 94 has not been activated, sequence proceeds to decision block 270, where it is determined whether the program button 96 has been activated. If so, the updated configuration of user preferences is stored in EEPROM 98 at step 276. Next, at step 278, the current parameters are changed to reflect the user preferences for those parameters that may be dynamically configured. Otherwise, the parameters will be updated then next time the recording unit 54 is powered up. Sequence 262 then reverts to decision block 170 as illustrated in FIG. 6. It should be appreciated that CPU 68 continues to interrupt sequence 262 at 480 Hz as described above and, thus, ECG data is continuously sampled functionally concurrently with programming sequence 262.

Alternatively, if the program button 96 is not activated at decision block 270, sequence 262 proceeds to decision block 274, where a timer (not shown) is examined to indicate whether a sufficient amount of time has passed since the last activation of either the store, send, or program buttons, thereby signifying a time-out status. If a time-out has not yet occurred, sequence 262 reverts once again to step 264. If, however, a time-out status exists, the sequence 262 will proceed to step 280 and return to decision block 170. Therefore, if so desired, the patient 50 may await the timeout and exit programming sequence 262 without saving the updated user preferences.

Referring once again to FIG. 6, it is determined at decision block 170 whether the patient has initiated an erase operation. In accordance with the preferred embodiment, an erase command is initiated by pressing and holding the STORE button for longer than 3 seconds after all stored events have been transmitted. A press for less than 3 seconds is recognized as a store command, as described above. It should be easily appreciated that a separate erase button could have been used in accordance with an alternate embodiment. Once the patient 50 initiates the erase operation, routine 142 proceeds to decision block 172 where it is determined whether all stored events have been transmitted to the remote terminal. If so, the event table 114 is cleared, and the memory is initialized as described above with reference to step 148. The routine 142 completes the steps while maintaining the current ECG data loop, thereby assuring that the patient 50 will not lose any data while clearing the memory. Alternatively, if the erase has not been initiated, or if all stored events have not been sent, the routine 142 will revert to process block 152 as described above.

The invention has been described in connection with what are presently considered to be the most practical and preferred embodiments. However, the present invention has been presented by way of illustration and is not intended to be limited to the disclosed embodiments. For example, it should be easily appreciated that, while a single memory is used to receive and store the ECG data, a memory could be implemented within the acquisition circuit to store ECG data while the processor is executing tasks such as transmitting the ECG data, setting user preferences, or operating after the transmission of ECG data. Accordingly, those skilled in the art will realize that the invention is intended to encompass all modifications and alternative arrangements included within the spirit and scope of the invention, as set forth by the appended claims.

What is claimed is:

1. An apparatus for recording electrocardiographic data from a patient, comprising:
   an acquisition circuit operable to receive at least one electrocardiographic signal having a time-varying amplitude from the patient at a plurality of instants in time to produce samples and further digitizing the samples of the electrocardiographic signal to indicate the amplitude of the electrocardiographic signal at the plurality of instants to produce digitized samples;
   at least one memory operable to receive and store the digitized samples according to their associated sampling instants in time; and
   a processor communicating with the acquisition circuit and the memory to transfer the digitized samples from the acquisition circuit to the memory as a first task while executing a second task on a functionally concurrent basis, wherein the second task is selected from the group consisting of transmitting electrocardiographic data and setting user preferences.

2. The apparatus as recited in claim 1, wherein the processor receives an interrupt at a frequency greater than the frequency at which the electrocardiographic data is sampled, and wherein the interrupt causes the processor to sample the electrocardiographic signal.

3. The apparatus as recited in claim 2, wherein the electrocardiographic signal is sampled at approximately 120 hertz, and the interrupt occurs at a frequency of approximately 480 hertz.

4. The apparatus as recited in claim 1, wherein the processor operates to continue to sample the electrocardiographic signal immediately after the data has been transmitted.

5. The apparatus as recited in claim 1, wherein an electrocardiographic event is detected and stored in the memory with the digitized samples so as to indicate relative ordering of the electrocardiographic event and the digitized samples.

6. The apparatus as recited in claim 1, wherein the second task comprises storing electrocardiographic data for future transmission.

7. The apparatus as recited in claim 6, wherein electrocardiographic data is stored in response to a manual input indicating an abnormal electrocardiographic event.

8. The apparatus as recited in claim 6, wherein the electrocardiographic data is stored in response to an automatic detection of an abnormal electrocardiographic event.

9. An apparatus for recording electrocardiographic data from a patient, comprising:

an acquisition circuit operable to receive at least one electrocardiographic signal having a time-varying amplitude from the patient at a plurality of instants in time to produce samples and further digitizing the samples of the electrocardiographic signal to indicate the amplitude of the electrocardiographic signal at the plurality of instants to produce digitized samples;

at least one memory operable to receive and store the digitized samples according to their associated sampling instants in time; and a processor communicating with the acquisition circuit and the memory to transfer the digitized samples from the acquisition circuit to the memory as a first task while executing a second task on a functionally concurrent basis, wherein the second task comprises operating at all points in time between the transmission of electrocardiographic data and erasure of the stored digitized samples.

10. A method for monitoring and transmitting electrocardiographic data from a patient to a remote display terminal, the steps comprising:

(a) receiving at least one electrocardiographic signal having a time-varying amplitude from the patient and transferring the signal to the apparatus;

(b) producing samples of the electrocardiographic signal at a plurality of instants;

(c) digitizing the samples to indicate the amplitude of the electrocardiographic signal at the plurality of instants;

(d) storing the digitized samples according to their associated sampling instants in time; and (e) performing at least one operation sequence on a functionally concurrent basis with step (d).

11. The method as recited in claim 10, further comprising detecting at least one cardiac abnormality and storing electrocardiographic data corresponding to the abnormality.

12. The method as recited in claim 11, wherein the at least one operation sequence includes one of the group consisting of transmitting the stored electrocardiographic data and setting at least one user preference.

* * * * *